United States Patent
Kellett

(10) Patent No.: US 11,174,560 B2
(45) Date of Patent: Nov. 16, 2021

(54) DBX-1, METHOD OF MANUFACTURE, AND DEVICE INCLUDING THE DBX-1

(71) Applicant: Ensign-Bickford Aerospace & Defense Company, Simsbury, CT (US)

(72) Inventor: Richard Kellett, Southwick, MA (US)

(73) Assignee: ENSIGN-BICKFORD AEROSPACE & DEFENSE COMPANY, Simsbury, CT (US)

( * ) Notice: Subject to any disclaimer, the term of this patent is extended or adjusted under 35 U.S.C. 154(b) by 396 days.

(21) Appl. No.: 16/407,241

(22) Filed: May 9, 2019

(65) Prior Publication Data

US 2020/0354842 A1    Nov. 12, 2020

(51) Int. Cl.
```
C25B 3/23      (2021.01)
C06B 25/34     (2006.01)
C07D 257/06    (2006.01)
```
(52) U.S. Cl.
CPC ............... *C25B 3/23* (2021.01); *C06B 25/34* (2013.01); *C07D 257/06* (2013.01)

(58) Field of Classification Search
CPC .............................. C06B 25/34; C07D 257/06
See application file for complete search history.

(56) References Cited

U.S. PATENT DOCUMENTS

| | | | |
|---|---|---|---|
| 9,440,934 B1 | 9/2016 | Mehta et al. | |
| 2013/0204005 A1* | 8/2013 | Fronabarger | C07D 257/06 |
| | | | 548/109 |
| 2015/0239910 A1* | 8/2015 | Klapotke | C07F 1/08 |
| | | | 548/107 |

OTHER PUBLICATIONS

Jorgensen, M., et al., "Development of a Lean Process to the Lead-Free Primary Explosive DBX-1" Organic Process Research & Development—May 2015 DOI: 10.1021/acs.oprd.5b00107.

Low, C. T. J., et al., "Copper deposition and dissolution in mixed chloride-sulphate acidic electrolytes: cyclic voltammetry at static disc electrode" (2015) Transactions of the iMF, 93:2, 74-81, DOI: 10.1179/0020296714Z.000000000220.

International Search Report and Written Opinion for International Application No. PCT/US2020/30384 dated Sep. 25, 2020; 14 pgs.

* cited by examiner

*Primary Examiner* — Salil Jain

(74) *Attorney, Agent, or Firm* — Cantor Colburn LLP

(57) ABSTRACT

A composition including copper(I) 5-nitrotetrazolate, wherein the composition has a carbon content of less than 7 weight percent, based on a total weight of the copper(I) 5-nitrotetrazolate.

4 Claims, 1 Drawing Sheet

DBX-1, METHOD OF MANUFACTURE, AND DEVICE INCLUDING THE DBX-1

BACKGROUND

(1) Field

Disclosed is a composition including copper(I) 5-nitrotetrazolate, methods for the manufacture of copper(I) 5-nitrotetrazolate, and a device including the copper(I) 5-nitrotetrazolate composition.

(2) Description of the Related Art

In military and commercial blasting, an explosive chain reaction is typically initiated by detonation of a small quantity of a highly sensitive primary explosive material. Commercially available primary explosives include lead(II) azide and lead(II) styphnate. Because of their lead content, lead(II) azide and lead(II) styphnate pose an environmental, health, and safety hazard.

Copper(I) 5-nitrotetrazolate (aka "DBX-1"), has proven to be a drop-in replacement for lead(II) azide in many existing detonator designs. DBX-1 has comparable explosive properties to lead(II) azide and avoids the toxicity and other drawbacks associate with lead. In spite of this, DBX-1 has made little progress in replacing lead(II) azide or lead(II) styphnate due to issues with its production. Thus there remains a need for an improved method to manufacture copper(I) 5-nitrotetrazolate.

SUMMARY

Disclosed is a composition including: copper(I) 5-nitrotetrazolate, wherein the composition has a carbon content of less than 7 weight percent, based on a total weight of the copper(I) 5-nitrotetrazolate.

Also disclosed is a method of manufacturing copper(I) 5-nitrotetrazolate, the method including: providing an electrochemical cell having a working electrode and a counter electrode, and an aqueous electrolyte disposed therein, wherein the aqueous electrolyte comprises $Cu^{2+}$, $SO_4^{2-}$, and a Group 17 anion; electrochemically reducing the $Cu^{2+}$ to form a $Cu^+$ species; and contacting the $Cu^+$ species with 5-nitrotetrazolate to form copper(I) 5-nitrotetrazolate.

Also disclosed is method of manufacturing copper(I) 5-nitrotetrazolate, the method including: providing an electrochemical cell having a working electrode comprising $Cu^0$ and a counter electrode, and an aqueous electrolyte disposed therein, wherein the aqueous electrolyte comprises $SO_4^{2-}$ and a Group 17 anion;
electrochemically oxidizing the $Cu^0$ to form a $Cu^+$ species; and contacting the $Cu^+$ species with 5-nitrotetrazolate to form copper(I) 5-nitrotetrazolate.

Also disclosed is a device including the composition.

BRIEF DESCRIPTION OF THE DRAWINGS

The above and other advantages and features of this disclosure will become more apparent by describing in further detail exemplary embodiments thereof with reference to the accompanying drawings, in which.

DETAILED DESCRIPTION

Figure 1:
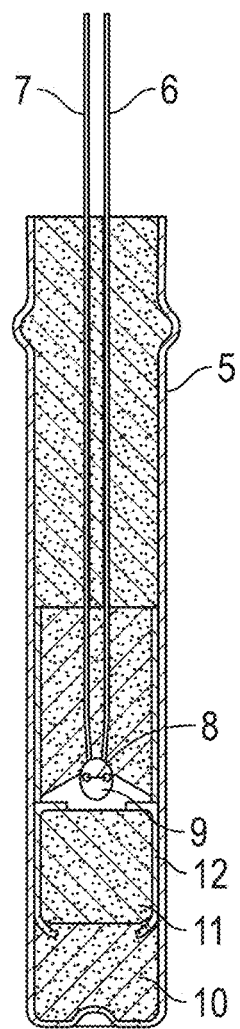
FIG. 1 is an aspect of a detonator.

Copper(I) 5-nitrotetrazolate (DBX-1) can be synthesized by reduction of sodium 5-nitrotetrazolate with sodium ascorbate in the presence of copper(II) chloride. By this method, formation of isolable crystals occurs unpredictably which not only limits production yields, but because of the nature of primary explosives, presents significant disposal and safety concerns. While not wanting to be bound by theory, it is understood that likely the non-isolable, poorly crystallized, material results from residual ascorbic acid, or decomposition products thereof, that remain in the product composition mixture.

It has been surprisingly discovered that $Cu^+$ is stable in aqueous solutions comprising $SO_4^{2-}$ and a Group 17 anion such as $Cl^-$. For example, and while not wanting to be bound by theory, it is understood that the $Cu^+$ species $CuCl_2^-$ is stable in an aqueous solution comprising $SO_4^{2-}$ and $Cl^-$, e.g., provided by dissolving $Na_2SO_4$ and $NaCl$ in water. It has also been discovered that the aqueous solution comprising the $Cu^+$ species can be contacted with 5-nitrotetrazolate to provide copper(I) 5-nitrotetrazolate (DBX-1), which is less soluble in water and thus can be isolated as a precipitate. The disclosed electrochemical method of DBX-1 synthesis avoids the use of the organic reducing agent that is believed to result occasionally in non-isolable DBX-1. In an aspect, $Cu^+$ is provided electrochemically and reacted with 5-nitrotetrazolate to provide DBX-1. The $Cu^+$ can be provided by electrochemical reduction of $Cu^{2+}$, or by electrochemical oxidation of $Cu^0$.

The disclosed method provides DBX-1 having improved properties. As noted above, and while not wanting to be bound by theory, it is understood that impurities from an organic reducing agent, e.g., ascorbic acid, likely results in unpredictable formation of non-isolable, poorly crystallized, material. Because the disclosed electrochemical method avoids the use of the organic reducing agent, such ascorbic acid, residual organic content in the DBX-1 reaction mixture solids is reduced. For example, the carbon content of the disclosed DBX-1 reaction mixture solids is less 7 weight percent (wt %), less than 6.9 wt %, 6.8 wt % to 20 wt %, 6.9 wt % to 15 wt %, or 7 wt % to 10 wt %, or 6.8 wt % to 6.85 wt %, or 6.81 wt % to 6.84 wt %, based on an total weight of the copper(I) 5-nitrotetrazolate. The carbon content can be determined by elemental analysis, for example. The DBX-1 having the disclosed carbon content can be reliably provided as a solid and formation of non-isolable, poorly crystallized material is avoided.

The content of ascorbate in the DBX-1 is less than 0.2 wt %, less than 0.1 wt %, less than 0.01 wt %, or 0 to 1 wt %, 0.001 wt % to 0.9 wt %, 0.01 wt % to 0.5 wt %, or 0.1 wt % to 0.4 wt %, based on an total weight of the copper(I) 5-nitrotetrazolate.

In an aspect, the disclosed method involves electrochemical reduction of $Cu^{2+}$ to $Cu^+$, as shown in Scheme 1, wherein X is an element of Group 17, e.g, F, Cl, Br, or I.

Scheme 1

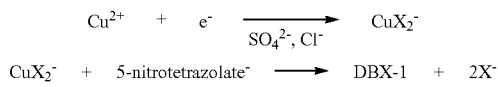

In further detail, disclosed is a method of manufacturing copper(I) 5-nitrotetrazolate. The method comprises providing an electrochemical cell having a working electrode and a counter electrode, and an aqueous electrolyte disposed therein, wherein the aqueous electrolyte comprises $Cu^+$, $SO_4^{2-}$, and a Group 17 anion; reducing the $Cu^{2+}$ to form a Cu⁺ species; and contacting the Cu⁺ species with 5-nitrotetrazolate to form copper(I) 5-nitrotetrazolate. Group, as used herein, refers to a Group of the Periodic Table of the Elements.

The electrochemical cell may be a cell suitable for laboratory synthesis, or may be a cell suitable for commercial production, such as a commercially available cell from Electrosynthesis, Co., of Lancaster, N.Y. The working electrode of the electrochemical cell may comprise a metal such as Pt, Pd, Au, or a combination thereof, carbon, or glassy carbon. A combination comprising at least one of the foregoing may be used. The counter electrode may comprise a metal such as Pt, Pd, Au, or a combination thereof, carbon, or glassy carbon. A combination comprising at least one of the foregoing may be used. Any suitable material for the working and counter electrodes may be used. Additional details of the electrochemical cell can be determined by one of skill in the art without undue experimentation, and thus will not be further elaborated upon herein for clarity.

In an aspect, an aqueous electrolyte comprising $Cu^{2+}$, $SO_4^{2-}$, and a Group 17 anion is disposed in the electrochemical cell. The $Cu^{2+}$ may be provided by dissolving a $Cu^{2+}$ compound in water. The $Cu^{2+}$ compound may be $CuSO_4$, a copper halide such as $CuCl_2$, $CuBr_2$, $CuI_2$, or a combination thereof, and maybe a hydrate thereof. A combination comprising at least one of the foregoing may be used. Any suitable source of $Cu^{2+}$ may be used. The $SO_4^{2-}$ may be provided by dissolving a $SO_4^{2-}$ compound in water. The $SO_4^{2-}$ compound may be an alkali metal sulfate, an alkaline earth metal sulfate, or an ammonium sulfate. A combination comprising at least one of the foregoing may be used. The $SO_4^{2-}$ compound may be a hydrate. Mentioned are $Li_2SO_4$, $Na_2SO_4$, $K_2SO_4$, $Rb_2SO_4$, $Cs_2SO_4$, $BeSO_4$, $MgSO_4$, $CaSO_4$, $SrSO_4$, $BaSO_4$, $(NH_4)_2SO_4$, or $CuSO_4$. The Group 17 anion may be provided by dissolving a Group 17 salt in water. The Group 17 anion may be an anion of an alkali metal salt, an alkaline earth metal salt, or an ammonium salt. A combination comprising at least one of the foregoing may be used. The Group 17 anion may be $F^-$, $Cl^-$, $Br^-$, or $I^-$. Mentioned are alkali metal and alkaline earth metal salts of $F^-$, $Cl^-$, $Br^-$, or $I^-$, such as LiF, NaF, KF, RbF, CsF, LiCl, NaCl, KCl, RbCl, CsCl, LiBr, NaBr, KBr, RbBr, CsBr, LiI, NaI, KI, RbI, CsI, $BeF_2$, $MgF_2$, $CaF_2$, $SrF_2$, $BaF_2$, $BeC_{12}$, $MgCl_2$, $CaCl_2$, $SrC_{12}$, $BaC_{12}$, $BeBr_2$, $MgBr_2$, $CaBr_2$, $SrBr_2$, $BaBr_2$, $BeI_2$, $MgI_2$, $CaI_2$, $SrI_2$, or $BaIe$. A combination comprising at least one of the foregoing may be used. NaCl is mentioned.

A content of the $Cu^{2+}$, $SO_4^{2-}$, and the Group 17 anion are selected to provide the desired reduction of $Cu^{2+}$ to form the $Cu^+$ species, and to provide for the stabilization of the $Cu^+$ species in the electrolyte. The concentration of $Cu^{2+}$, $SO_4^{2-}$, and the Group 17 anion may each be independently selected and may each be 0.01 moles per liter (M) to 10 M, 0.1 M to 5 M, 0.2 M to 1 M. Use of 0.5 M $Na_2SO_4$, 2 M NaCl, and 0.1 M $CuSO_4$ is mentioned.

The $Cu^{2+}$ may be electrochemically reduced to form a $Cu^+$ species by applying a suitable potential at the working electrode. A suitable potential is a potential which provides for reduction of the $Cu^{2+}$ to $Cu^t$, and avoids alternative products, such as $Cu^0$. Relative to a Ag/AgCl reference electrode, the electrochemical reduction of the $Cu^{3+}$ may be accomplished by applying a potential of greater than −0.2 volts (V) to the working electrode, versus a Ag/AgCl reference electrode. The potential at the working electrode may be −0.2 V to 0.5 V, −0.15 V to 0.4 V, or −0.1 V to 0.3 V, each versus Ag/AgCl.

While not wanting to be bound by theory, it is understood that reduction of $Cu^{2+}$ to $Cu^+$ in the disclosed electrolyte results in soluble a Cu(I) Group 17 compound, e.g., $CuCl_2^-$, in an aspect where the Group 17 anion is $Cl^-$.

Contacting the solution of Cu(I) Group 17 compound, e.g., $CuCl_2^-$, with 5-nitrotetrazolate provides copper(I) 5-nitrotetrazolate. The copper(I) 5-nitrotetrazolate precipitates, permitting isolation of the DBX-1. Isolation may comprise filtration or centrifugation, for example. The contacting may comprise combining a stream comprising the solution of the Cu(I) Group 17 compound, e.g., $CuCl_2^-$, and a stream comprising 5-nitrotetrazolate. Combining the Cu(I) Group 17 compound and the stream comprising 5-nitrotetrazolate may provide additional benefits, such as improved safety, for example.

In an aspect, $Cu^0$ can be electrochemically oxidized to provide a $Cu^+$ species, and the $Cu^+$ species contacted with 5-nitrotetrazolate to form copper(I) 5-nitrotetrazolate, as shown in Scheme II, wherein X is an element of Group 17, e.g., F, Cl, Br, or I.

Scheme II.

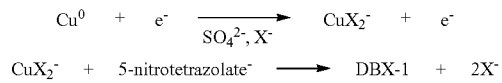

$$Cu^0 + e^- \xrightarrow{SO_4^{2-}, X^-} CuX_2^- + e^-$$

$$CuX_2^- + \text{5-nitrotetrazolate}^- \longrightarrow DBX\text{-}1 + 2X^-$$

In further detail, disclosed is a method of manufacturing copper(I) 5-nitrotetrazolate comprising: providing an electrochemical cell having a working electrode comprising $Cu^0$ and a counter electrode, and an aqueous electrolyte disposed therein, wherein the aqueous electrolyte comprises $SO_4^{2-}$ and a Group 17 anion; electrochemically oxidizing the $Cu^0$ to form a $Cu^+$ species; and contacting the $Cu^+$ species with 5-nitrotetrazolate to form copper(I) 5-nitrotetrazolate.

An aqueous electrolyte comprising $SO_4^{2-}$ and the Group 17 anion is disposed in the electrochemical cell. The $SO_4^{2-}$ may be provided by dissolving a $SO_4^{2-}$ compound in water. As noted above, the $SO_4^{2-}$ compound may be an alkali metal sulfate, an alkaline earth metal sulfate, or an ammonium sulfate. A combination comprising at least one of the foregoing may be used. Any suitable cation, such as $Na^+$ or $NH_4^+$, may be used. Mentioned are $Li_2SO_4$, $Na_2SO_4$, $K_2SO_4$, $Rb_2SO_4$, $Cs_2SO_4$, $BeSO_4$, $MgSO_4$, $CaSO_4$, $SrSO_4$, $BaSO_4$, $(NH_4)_2SO_4$, or $CuSO_4$. As noted above, the Group 17 anion may be provided by dissolving a Group 17 salt in water. The Group 17 anion may be an anion of an alkali metal salt, an alkaline earth metal salt, or an ammonium salt. A combination comprising at least one of the foregoing may be used. The Group 17 anion may be $F^-$, $Cl^-$, $Br^-$, or $I^-$. Mentioned are alkali metal and alkaline earth metal salts of $F^-$, $Cl^-$, Br, or $I^-$, such as LiF, NaF, KF, RbF, CsF, LiCl, NaCl, KCl, RbCl, CsCl, LiBr, NaBr, KBr, RbBr, CsBr, LiI, NaI, KI, RbI, CsI, $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, or $BaI_2$. A combination comprising at least one of the foregoing may be used. NaCl is mentioned. The electrolyte may further comprise a $Cu^+$ species. The $Cu^+$ species can be provided by oxidation of $Cu^0$. Alternatively, or in addition, the $Cu^+$ species may be provided by including a Cu(I) salt, such as a Cu(I) halide, e.g., CuF, CuBr, CuCl, or CuI, in the electrolyte. Any of the foregoing compounds or salts may be a hydrate, if desired.

A content of the $Cu^+$, $SO_4^{2-}$, and the Group 17 anion in the electrolyte are selected to provide the desired stabilization of $Cu^+$, e.g., the $Cu^+$ species, in the electrolyte. The concentration of $Cu^+$, $SO_4^{2-}$, and the Group 17 anion may each be independently selected and may each be 0.01 moles per liter (M) to 10 M, 0.1 M to 5 M, 0.2 M to 1 M. Use of 0.5 M $Na_2SO_4$, 2 M NaCl, and 0.1 M $CuSO_4$ is mentioned.

In an aspect, the working electrode comprises $Cu^0$, consists of $Cu^0$, or an alloy thereof. Also disclosed is a working electrode in which $Cu^0$ is disposed on a suitable inert support, such as a porous nickel support.

The $Cu^0$ may be electrochemically oxidized to form a $Cu^+$ species by applying a suitable potential at the working electrode. A suitable potential is a potential which provides for oxidation of the $Cu^0$ to $Cu^+$, and avoids alternative products, such as $Cu^{2+}$. Relative to a Ag/AgCl reference electrode, the electrochemical oxidation of $Cu^0$ may be accomplished by applying a potential of greater than −0.2 volts (V) versus a Ag/AgCl reference electrode to the working electrode. The potential at the working electrode may be −0.2 V to 0.5 V, −0.15 V to 0.4 V, or −0.1 V to 0.3 V, each versus Ag/AgCl.

Electrochemical potentials are disclosed relative to Ag/AgCl for convenience. A different reference electrode could be used, e.g., a standard hydrogen electrode, and the applied potential adjusted accordingly to provide the disclosed absolute potential, i.e., a same electrochemical driving force.

Also disclosed is a device comprising the composition, i.e., the DBX-1. The device may be a munition or a component thereof, such as a detonator. With reference to FIG. 1, The detonator may comprise a shell 5, wires 6 and 7, and a bridge wire 8 embedded in a composition 9 comprising or consisting of the DBX-1. If desired, the detonator may contain an additional composition, e.g., additional compositions 10 or 11, which may be provided in a capsule 12.

The invention has been described with reference to the accompanying drawings, in which various aspects are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an."

"Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

PROPHETIC EXAMPLES

Prophetic Example 1: Synthesis of DBX-1 by $Cu^{2+}$ Reduction, 2 Steps

NaCl (2 moles per liter (M)), $Na_2SO_4$ (0.5 M), and $CuSO_4$-$(H_2O)_5$ (0.1 M) will be dissolved in water to provide an aqueous solution.

Figure 2:
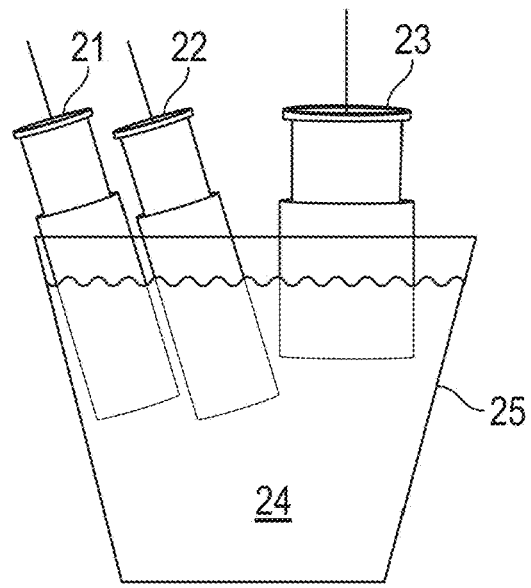
FIG. 2 is an aspect of an electrochemical reactor.

The aqueous solution 24 will be disposed in a three electrode glass reactor 25 (Pine Research Instrumentation) fitted with a platinum working electrode 21, a glassy carbon counter electrode 23 and a Ag/AgCl reference electrode 22 as shown in FIG. 2.

An electric potential will be applied between the working and counter electrodes to provide a potential of 0.1 volts versus Ag/AgCl at the working electrode.

A solution containing 5-nitrotetrazolate will be added, resulting in the formation of a solid, which will precipitate from the aqueous solution. The precipitate will be isolated by filtration. Analysis will show the precipitate to be copper (I) 5-nitrotetrazolate.

Prophetic Example 2: Synthesis of DBX-1 by $Cu^{2+}$ Reduction, 1 Step

NaCl (2 moles per liter (M)), $Na_2SO_4$ (0.5 M), $CuSO_4$-$(H_2O)_5$ (0.1 M), and 5-nitrotetrazolate (0.1 M) will be dissolved in water to provide an aqueous solution.

The aqueous solution will be disposed in the three electrode glass reactor described above, fitted with a platinum working electrode, a glassy carbon counter electrode and a Ag/AgCl reference electrode.

An electric potential will be applied between the working and counter electrodes to provide a potential of 0.1 volts versus Ag/AgCl at the working electrode.

A solid will form, which will precipitate from the aqueous solution. The precipitate will be isolated by filtration. Analysis will show the precipitate to be copper(I) 5-nitrotetrazolate.

Prophetic Example 3: Synthesis of DBX-1 by $Cu^0$ Oxidation

NaCl (2 moles per liter (M)) and $Na_2SO_4$ (0.5 M) will be dissolved in water to provide an aqueous solution.

The aqueous solution will be disposed in a three electrode glass reactor described above, fitted with a copper working electrode, a glassy carbon counter electrode and a Ag/AgCl reference electrode.

An electric potential will be applied between the working and counter electrodes to provide a potential of 0.1 volts versus Ag/AgCl at the working electrode.

A solution containing 5-nitrotetrazolate will be added to the reactor, resulting in the formation of a solid, which will precipitate from the aqueous solution. The precipitate will be isolated by filtration. Analysis will show the precipitate to be copper(I) 5-nitrotetrazolate.

The disclosed aspects described herein shall be considered in a descriptive sense only and not for purposes of limitation. Descriptions of features or aspects within each embodiment should be considered as available for other similar features or aspects in other exemplary embodiments. While an aspect has been described with reference to the figures, it will be understood by those of ordinary skill in the art that various changes in form and details may be made therein without departing from the spirit and scope as defined by the following claims.

What is claimed is:

1. A method of manufacturing copper(I) 5-nitrotetrazolate, the method comprising:
   providing an electrochemical cell having a working electrode comprising $Cu^0$ and a counter electrode, and an aqueous electrolyte disposed therein, wherein the aqueous electrolyte comprises $SO_4^{2-}$ and a Group 17 anion;
   electrochemically oxidizing the $Cu^0$ to form a $Cu^+$ species; and
   contacting the $Cu^+$ species with 5-nitrotetrazolate to form copper(I) 5-nitrotetrazolate.

2. The method of claim 1, wherein the Group 17 anion is $Cl^-$, the $Cu^+$ species is $CuCl_2^-$, and further comprising isolating a solution comprising the $CuCl_2^-$, and then
   contacting the solution comprising $CuCl_2^-$ with 5-nitrotetrazolate to form the copper(I) 5-nitrotetrazolate.

3. The method of claim 1, wherein the oxidizing comprises oxidizing at a potential of less than 0.2 volts versus Ag/AgCl.

4. A device comprising the copper(I) 5-nitrotetrazolate product of claim 2.

* * * * *